(12) United States Patent
Breed et al.

(10) Patent No.: US 8,017,812 B2
(45) Date of Patent: Sep. 13, 2011

(54) PROCESS FOR THE LIQUID PHASE OXIDATION OF ETHYLBENZENE INTO ETHYLBENZENE HYDROPEROXIDE

(75) Inventors: Anthonius Johannes Maria Breed, Amsterdam (NL); Andrew David Horton, Amsterdam (NL); Peter Anton August Klusener, Amsterdam (NL)

(73) Assignee: Shell Oil Company, Houston, TX (US)

( * ) Notice: Subject to any disclaimer, the term of this patent is extended or adjusted under 35 U.S.C. 154(b) by 553 days.

(21) Appl. No.: 11/938,577

(22) Filed: Nov. 12, 2007

(65) Prior Publication Data

US 2008/0188674 A1 Aug. 7, 2008

(30) Foreign Application Priority Data

Nov. 13, 2006 (EP) .................................. 06123925

(51) Int. Cl.
*C07C 409/00* (2006.01)

(52) U.S. Cl. ...................................................... 568/571

(58) Field of Classification Search .................... 568/571
See application file for complete search history.

(56) References Cited

U.S. PATENT DOCUMENTS

| 3,459,810 | A | * | 8/1969 | Choo et al. | ..................... | 568/569 |
| 4,066,706 | A | * | 1/1978 | Schmidt | ........................ | 568/569 |
| 4,602,118 | A | | 7/1986 | Chou et al. | ...................... | 568/570 |
| 4,956,327 | A | * | 9/1990 | Erekson et al. | ............... | 502/216 |

OTHER PUBLICATIONS

EPA-454/R-93-011 (1993).*
Kulicka et al DN 67:104940 (1967).*

* cited by examiner

*Primary Examiner* — Andrew D. Kosar

(57) ABSTRACT

The invention relates to a process for the liquid phase oxidation of ethylbenzene into ethylbenzene hydroperoxide, wherein the ethylbenzene hydroperoxide concentration is kept below 20 wt. % on the basis of the total weight of the reaction mixture, and wherein styrene and/or a styrene derivative is fed to the ethylbenzene. The concentration of said styrene and/or a styrene derivative may be from 0.01 to 5.0 wt. %.

11 Claims, 2 Drawing Sheets

PROCESS FOR THE LIQUID PHASE OXIDATION OF ETHYLBENZENE INTO ETHYLBENZENE HYDROPEROXIDE

This application claims the benefit of an earlier filed foreign application, European Application No. 06123925.7, filed on Nov. 13, 2006, which is hereby incorporated by reference.

FIELD OF THE INVENTION

The present invention relates to a process for the liquid phase oxidation of ethylbenzene into ethylbenzene hydroperoxide.

BACKGROUND

Ethylbenzene hydroperoxide can be prepared by the liquid phase oxidation of ethylbenzene with oxygen containing gas, such as air. Such oxidation processes are well known in the art. An example thereof is described in U.S. Pat. No. 5,883,268.

In such oxidation reaction of ethylbenzene, methyl phenyl carbinol (1-phenylethanol) and methyl phenyl ketone (acetophenone) are formed as side-products. Subsequent oxidation of an alkene (such as propene) with the ethylbenzene hydroperoxide results in the production of alkene oxide (an oxirane or epoxide; such as propylene oxide) and methyl phenyl carbinol. Methyl phenyl ketone can be converted with hydrogen into methyl phenyl carbinol. Methyl phenyl carbinol can be dehydrated into styrene. Both the styrene and the propylene oxide are valuable market products.

Processes for the joint preparation of styrene monomer ("SM") and propylene oxide ("PO") are known in the art and are commonly referred to as "SM/PO" processes. An SM/PO process is for example described in WO 00/05186. In general, an SM/PO process comprises the steps of:
(a) reacting ethene and benzene to form ethylbenzene,
(b) reacting ethylbenzene with oxygen containing gas to form ethylbenzene hydroperoxide,
(c) reacting ethylbenzene hydroperoxide with propene in the presence of an epoxidation catalyst to form propylene oxide and 1-phenylethanol, and
(d) dehydrating 1-phenylethanol into styrene in the presence of a suitable dehydration catalyst.

During said steps (b) and (c), methyl phenyl ketone is formed as a side-product. Prior to said step (d), this methyl phenyl ketone may be converted with hydrogen to methyl phenyl carbinol (1-phenylethanol).

During said step (b) of oxidising ethylbenzene into ethylbenzene hydroperoxide, not all ethylbenzene reacts. Said unreacted ethylbenzene may be recycled to the oxidation reactor. The oxidation reaction is carried out at a concentration below 20 wt. % of ethylbenzene hydroperoxide on the basis of the total weight of the reaction mixture. In general, at or above this concentration, the production of the side-products methyl phenyl carbinol and methyl phenyl ketone grows relative to the amount of ethylbenzene hydroperoxide, causing inefficient loss of reactant ethylbenzene.

Hence, the concentration of ethylbenzene hydroperoxide in the reaction mixture is kept relatively low. There is a continuing desire among those skilled in the art to achieve a high oxidation rate when working under the above maximum ethylbenzene hydroperoxide concentration.

SUMMARY OF THE INVENTION

It has now been found that, although the presence of styrene slows down the oxidation of ethylbenzene to ethylbenzene hydroperoxide when ethylbenzene hydroperoxide is present at a concentration of 20 wt. % or higher, feeding a relatively small amount of styrene and/or a styrene derivative to the ethylbenzene, has a promoting effect when the ethylbenzene hydroperoxide concentration is below 20 wt. %. Therefore, a recycle stream of ethylbenzene may advantageously contain styrene and/or a styrene derivative as a contaminant, making extensive purification steps no longer necessary.

The above finding is even more surprising, when it is considered that in the art it was generally thought that styrene and styrene derivatives, such as α-methylstyrene, would have a inhibitory effect on the oxidation of alkylaryl compounds, such as cumene (isopropylbenzene), s-butylbenzene, etc. For example, G. A. Russell discloses in J. Am. Chem. Soc. 77, 4583-4590, 1955, that styrene retards the oxidation of cumene. α-Methylstyrene would have no effect when added to cumene: that is to say, no inhibitory effect on cumene oxidation was observed by Russell. G. P. Armstrong et al., in J. Chem. Soc., 666-670, 1950, disclosed that both styrene and α-methylstyrene retarded the oxidation of cumene. In view of the foregoing, it is quite unexpected and surprising that the present inventors have found that in the oxidation of ethylbenzene (an alkylaryl compound), styrene and styrene derivatives do not have an inhibitory effect but have in fact a promoting effect on the oxidation, thereby achieving a high oxidation rate as desired.

Accordingly, the present invention relates to a process for the liquid phase oxidation of ethylbenzene into ethylbenzene hydroperoxide, wherein the ethylbenzene hydroperoxide concentration is kept below 20 wt. % on the basis of the total weight of the reaction mixture, and wherein styrene and/or a styrene derivative is fed to the ethylbenzene. Said styrene and/or a styrene derivative may be fed to the ethylbenzene prior to or during its oxidation. Further, it may be fed to the ethylbenzene both prior to and during its oxidation.

DETAILED DESCRIPTION OF THE INVENTION

Figure 1:
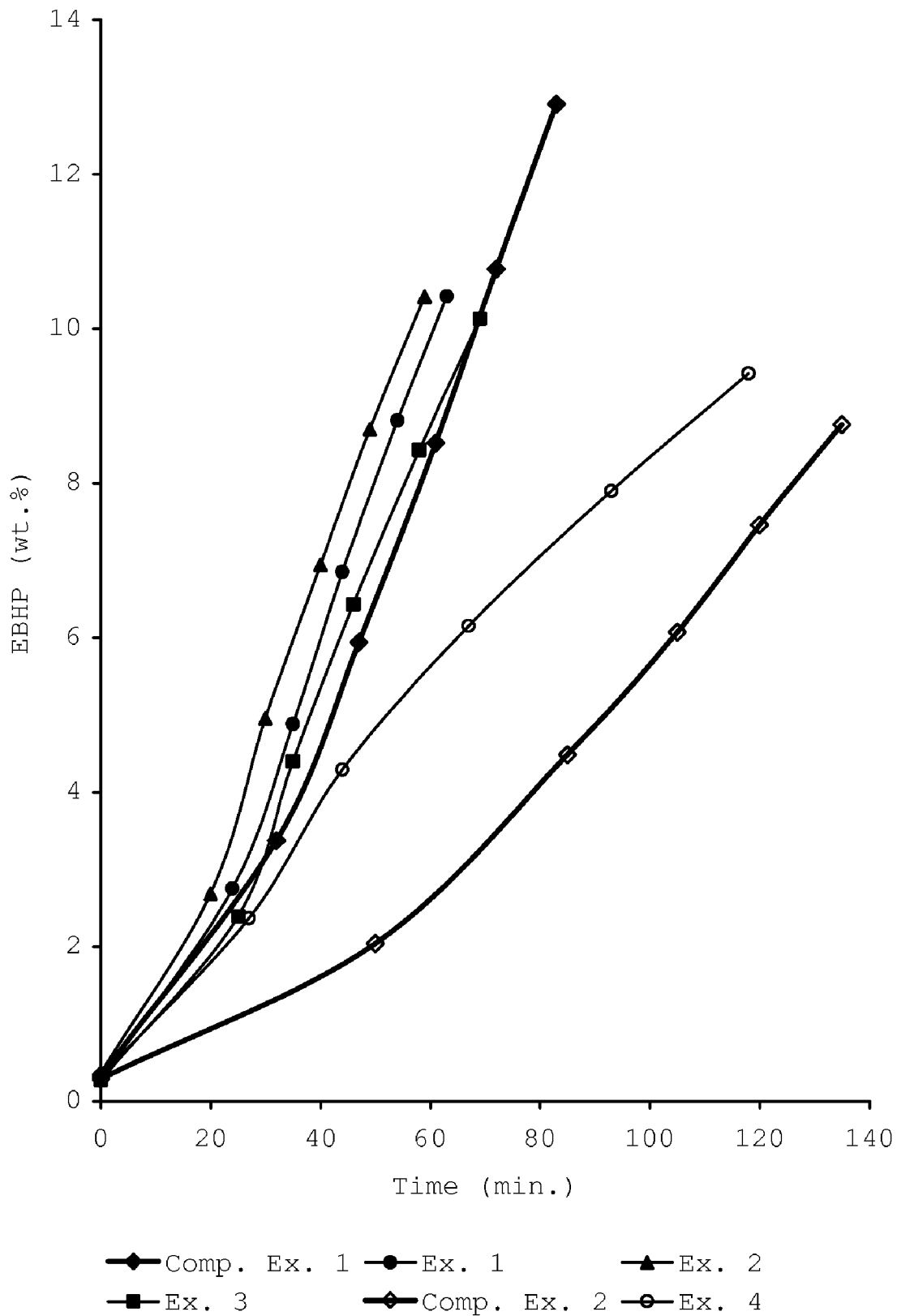
FIG. 1 depicts the production of ethylbenzene hydroperoxide as a function of time.

The oxidation in the process according to the invention can be carried out by any suitable process known in the art wherein the oxidisable compound (ethylbenzene) is in the liquid phase and the oxidant is an oxygen containing gas. In general, this liquid phase oxidation of ethylbenzene into ethylbenzene hydroperoxide is carried out at a temperature of from 50 to 250° C., suitably of from 100 to 200° C., and more suitably of from 120 to 180° C. The reactor vessel will generally contain a heat exchanger so as to heat the reaction mixture at the start of operation and to cool when the reaction has progressed sufficiently.

The amount of oxygen to be added and the amount of ethylbenzene to be added depend on the specific circumstances of the process such as the volume and shape of the reactor vessel and the concentration of hydroperoxide which, in accordance with the present invention, should be kept below 20 wt. % on the basis of the total weight of the reaction mixture. Suitably, the ethylbenzene hydroperoxide concentration in the reaction mixture is lower than 15 wt. %, preferably lower than 12 wt. %. The ethylbenzene hydroperoxide concentration in the reaction mixture may be in the range of from 10 to 15 wt. %, preferably from 10 to 12 wt. %.

The pressure of the present process is not critical and can be chosen such as to best accommodate specific circumstances. Generally, the pressure near the top of the reactor vessel will be from atmospheric to $10*10^5$ N/m$^2$, more specifically from 1 to $5*10^5$ N/m$^2$.

The oxidation of ethylbenzene is carried out in the liquid phase and can be carried out in the presence of a diluent. This diluent is preferably a compound which is liquid under the reaction conditions and does not react with the starting materials and product obtained. The diluent can be ethylbenzene itself. In a preferred embodiment, the process of the present invention can be used to prepare a solution of ethylbenzene hydroperoxide in ethylbenzene.

After discharge from the reactor vessel, the reaction mixture is separated into (i) a product stream containing ethylbenzene hydroperoxide dissolved in ethylbenzene wherein the ethylbenzene hydroperoxide concentration may be from 20 to 50 wt. %, and (ii) an ethylbenzene stream. Such separation may be effected by flash distillation wherein part of the ethylbenzene is distilled overhead.

Since a relatively large amount of ethylbenzene is not reacted in the oxidation, ethylbenzene is generally recycled to the inlet of the oxidation reactor, after having removed the contaminants from such recycle stream. One of the contaminants contained in such recycle ethylbenzene feed in integrated processes for producing an alkylene oxide (for example propylene oxide), using ethylbenzene hydroperoxide, and styrene (for example the SM/PO process), may be styrene. The present invention obviates the need for removing styrene, if present, from such recycle ethylbenzene feed. In fact, said styrene can advantageously be used as a promoting substance in the oxidation of ethylbenzene. In such case, extensive purification steps to remove the styrene are no longer necessary. Therefore, it is preferred to feed styrene to the ethylbenzene, preferably via a recycle ethylbenzene stream containing styrene as a contaminant.

The process according to the present invention may be carried out continuously. In general, the reactor vessel used in a continuous process for oxidation of ethylbenzene, is provided with a liquid inlet at one end and a fluid outlet at the opposite end. Further, the lower part of the reactor vessel generally contains a gas inlet device, which may be a sparge pipe (or perforated pipe). Normally, the gas is removed together with the liquid, via the fluid outlet. However, dependent on the exact circumstances, it can be advantageous to remove excess gas via a separate gas outlet during normal operation. One or more separate gas outlets can be present. Normally, the fluid outlet is at the bottom of the vessel and the optional gas outlet at the top of the vessel. However, this is not required. The preferred height at which each outlet is situated depends on a number of factors as will be appreciated by someone skilled in the art. One of these circumstances is the level which the liquid generally reaches.

The gas removed via said one or more gas outlets of the oxidation reactor vessel can contain a considerable amount of ethylbenzene vapor. The exact amount depends on the process conditions applied. If desirable, the ethylbenzene vapor can be condensed into liquid ethylbenzene and recycled.

It has been found that not only styrene promotes the oxidation of ethylbenzene, but that derivatives of styrene also have such an effect. Within the context of the present invention, styrene derivatives may be compounds containing a benzene core to which is directly bonded one ethenyl group and to which are directly bonded one or more further substituents. Further, within the context of the present invention, the ethenyl group of the styrene and said styrene derivatives may be substituted. Said ethenyl group may be substituted by an alkyl group and/or a halogen atom. Preferably, such alkyl group is a straight or branched alkyl group comprising from 1 to 10 carbon atoms, more preferably 1 to 5 carbon atoms, and may for example be a methyl, ethyl, n-propyl, i-propyl, n-butyl, s-butyl or t-butyl group. The alkyl group or alkyl groups may be attached to the carbon atoms on the α and/or β position of the styrene core. Examples of such styrene derivatives, useful in the present invention, are α-methylstyrene, α-ethylstyrene, and α,β-dimethylstyrene, which latter compound may be present as a mixture of two geometric isomers.

In accordance with the invention, styrene derivatives may thus comprise styrene derivatives wherein one or more of the unsubstituted carbon atoms of styrene is or are substituted by an alkyl group and/or a halogen atom. Preferably, such alkyl group is a straight or branched alkyl group comprising from 1 to 10 carbon atoms, more preferably 1 to 5 carbon atoms, and may for example be a methyl, ethyl, n-propyl, i-propyl, n-butyl, s-butyl or t-butyl group. The halogen atom in said styrene derivatives may be a fluorine, chlorine, bromine or iodine atom.

Any carbon atom of the styrene core in the above-mentioned styrene derivatives, other than that carbon atom to which the ethenyl group is attached, may be substituted with said alkyl group and/or halogen atom. The carbon atom on the para-position relative to the substituted carbon atom of styrene, may for example be substituted. Examples of such styrene derivatives, useful in the present invention, are 4-t-butylstyrene and 4-chlorostyrene.

Preferably, during the start-up phase (induction period) of the oxidation reaction, a small amount of an organic peroxide, such as ethylbenzene hydroperoxide itself, is added as an initiator to the ethylbenzene. The amount of ethylbenzene hydroperoxide to be added should be such that the oxidation of ethylbenzene is started. The amount of ethylbenzene hydroperoxide may be of from 0.1 to 2.0 wt. %, suitably from 0.25 to 1.0 wt. %, based on the weight of the total reaction mixture.

The amount of styrene and/or styrene derivatives to be fed in the present process should be such that the amount of styrene and/or styrene derivatives in the reaction mixture is a promoting amount. More specifically, said amount should preferably be such that a particular conversion is achieved within a shorter time period in comparison with the situation where no styrene and/or styrene derivatives are fed.

Preferably, the amount of styrene and/or styrene derivatives to be fed in the present process is such that the concentration of styrene and/or styrene derivatives in the reaction mixture, on the basis of the total weight of the reaction mixture, is at least 0.01 wt. %, more preferably at least 0.03 wt. %, more preferably at least 0.05 wt. %, more preferably at least 0.075 wt. %, more preferably at least 0.1 wt. %, more preferably at least 0.3 wt. %, more preferably at least 0.5 wt. %, more preferably at least 0.7 wt. %, more preferably at least 0.9 wt. % and most preferably at least 1.0 wt. %. Further, preferably, the amount of styrene and/or styrene derivatives to be fed in the present process is such that the concentration of styrene and/or styrene derivatives in the reaction mixture, on the basis of the total weight of the reaction mixture, is at most 5.0 wt. %, more preferably at most 4.0 wt. %, more preferably at most 3.5 wt. %, more preferably at most 3.0 wt. %, more preferably at most 2.5 wt. %, more preferably at most 2.0 wt. %, more preferably at most 1.7 wt. % and most preferably at most 1.5 wt. %. Suitably, the concentration of styrene and/or styrene derivatives in the reaction mixture is comprised within the range of from 0.01 to 5.0 wt. %, preferably 0.05 to 3.0 wt. %, and most preferably 0.1 to 2.0 wt. %, on the basis of the total weight of the reaction mixture.

The oxidation is carried out by feeding an oxygen containing gas to the reaction mixture as a gas inlet stream. The oxygen concentration in the gas feed may be from 5 to 100 vol. %, suitably from 10 to 60 vol. %, more suitably from 20 to 50 vol. %, wherein the remainder is preferably an inert gas such as nitrogen. Air, which on average contains 21 vol. % of oxygen is the preferred oxygen containing gas feed. The temperature of the gas at the gas inlet may be from ambient temperature to 250° C.

The temperature of the gas in the gas outlet stream is normally higher than ambient temperature and may be as high as the reactor temperature. To avoid the risk of explosion, the oxygen concentration in the gas outlet stream, after cooling to ambient temperature, is normally lower than 10 vol. %, suitably lower than 8 vol. %, and more suitably lower than 7 vol. %. For example, the gas outlet stream may comprise 5 vol. % of oxygen.

The oxygen containing gas may be introduced into the oxidation reactor in any way, for example by means of sparge pipes. Sparge pipes (or perforated pipes), which are normally mounted at the bottom of the oxidation reactor, comprise openings or holes in their walls through which the oxygen containing gas may be fed into the reaction mixture.

The present process may be carried out continuously. In such continuous process, the oxidation reactor is preferably horizontally oriented which means that the stream of reaction mixture flows horizontally through the reactor. Preferably, where the oxidation reactor is horizontally oriented, a substantially horizontal reactor vessel is used having a lower part and two opposite ends, which reactor vessel comprises a liquid inlet at one end, a fluid outlet at the opposite end and a gas inlet device arranged in the lower part, which reactor vessel contains at least one substantially vertical baffle-plate arranged in the direction of liquid flow through the reactor vessel during normal operation. Such a reactor vessel is disclosed in WO 2006/024655, and the reactor vessel disclosed therein may be used in the present invention.

Further, in such continuous process, the oxidation reactor may be comprised of two or more separate reaction zones (sometimes also referred to as separate compartments). Alternatively, two or more oxidation reactors arranged in series may be used of which some or all may be comprised of two or more separate reaction zones. In such case, the fluid outlet of one reactor vessel is connected to the liquid inlet of a subsequent reactor vessel.

Where the oxidation reactor is comprised of two or more separate reaction zones, the stream of reaction mixture flows from the first reaction zone to the second reaction zone and from said second reaction zone to a further reaction zone or to a further reactor or to a separation unit. The reaction zones can differ from each other in various aspects such as the degree of conversion, which has taken place. The separate reaction zones can be created in a single reactor vessel by means which are known to someone skilled in the art. A very well known means to achieve this involves placing a vertical plate between the reaction zones perpendicular to the direction of flow such that the plate has an opening which permits fluid to flow from one reaction zone to the subsequent reaction zone. A detailed set-up of a single reactor vessel containing a plurality of reaction zones has been described in U.S. Pat. No. 4,269,805. Such a reactor vessel can be used in the present invention.

The ethylbenzene hydroperoxide obtained in the present process can advantageously be used in processes for the preparation of alkylene oxides from alkenes. The alkene used in such processes is preferably an alkene comprising from 2 to 10 carbon atoms and more preferably an alkene comprising from 2 to 4 carbon atoms. Examples of alkenes that can be used include ethene, propene, 1-butene and 2-butene, with which the corresponding ethylene oxide, propylene oxide and butylene oxides can be prepared.

In an additional process step, the ethylbenzene hydroperoxide obtained from the process as described above, is contacted with an alkene to obtain an alkylene oxide. In this additional step, the ethylbenzene hydroperoxide itself is converted into methyl phenyl carbinol (1-phenylethanol). Preferably, this reaction is carried out in the presence of a catalyst. A preferred catalyst for such process comprises titanium on silica and/or silicate. Further preferred catalysts are described in EP-A-345856. The reaction generally proceeds at moderate temperatures and pressures, in particular at temperatures in the range of from 25 to 200° C., preferably in the range from 40 to 135° C. The precise pressure is not critical as long as it suffices to maintain the reaction mixture as a liquid or as a mixture of vapour and liquid. In general, pressures can be in the range of from 1 to 100 bar, preferably in the range from 20 to 80 bar.

The alkylene oxide can be separated from the reaction product in any way known to be suitable to someone skilled in the art. For example, the liquid reaction product may be worked up by fractional distillation and/or selective extraction. The solvent, the catalyst and any unreacted alkene or hydroperoxide may be recycled for further utilization.

In a further additional process step, the 1-phenylethanol, once separated from the reaction mixture, is converted into styrene by dehydration. As discussed above, said 1-phenylethanol may originate from the alkene epoxidation reaction using ethylbenzene hydroperoxide, but also from oxidizing ethylbenzene and/or from hydrogenating methyl phenyl ketone which is formed as a side-product. It is preferred to convert all of the 1-phenylethanol produced in said different steps, in only one dehydration step.

Processes which can be used for the step of dehydrating 1-phenylethanol have been described in WO 99/42425 and WO 99/42426. However, any suitable process known to someone skilled in the art can in principle be used.

Accordingly, the present invention also relates to a process for the preparation of an alkylene oxide and styrene, comprising the steps of:
 i) oxidizing ethylbenzene into ethylbenzene hydroperoxide according to the process as described above;
 ii) reacting the ethylbenzene hydroperoxide with an alkene to prepare alkylene oxide and methyl phenyl carbinol; and
 iii) dehydrating methyl phenyl carbinol into styrene. Preferably, said alkene is propylene.

The invention is further illustrated by the following Examples.

COMPARATIVE EXAMPLE 1

One kg of ethylbenzene, having a styrene content <100 mg/kg, was placed in a 2 litre glass reactor vessel, which was provided with a stirrer, a gas inlet at the bottom, and a gas outlet. The gas outlet was combined with a reflux condenser.

The ethylbenzene hydroperoxide concentration in the reactor content was brought to a certain amount as indicated in Table 1 using a 35 wt. % stock solution of ethylbenzene hydroperoxide in ethylbenzene. The reactor vessel was pressurized with nitrogen to 2.9 bar, and the reactor content was heated to 156° C. As soon as this temperature was reached, an air/nitrogen gas mixture was fed into the reactor vessel, while vigorous stirring was applied and the reactor temperature was kept constant at 156° C. The total gas flow was kept at 110 litres/hr (under normal conditions). The experiment was carried out in semi-continuous batch mode in which said gas mixture was fed continuously.

The reflux temperature in the reflux condenser was kept at 95° C. thereby condensing any entrained organic compounds. After passing the reflux condenser, the gas outlet flow was further cooled by a cold trap at −78° C. After passing the cold trap, the gas outlet flow was warmed up to ambient temperature, and was then sent to an analyser measuring the oxygen concentration. The air/nitrogen ratio in the gas inlet flow was adjusted such that the oxygen concentration in the cooled gas outlet flow was kept at 4.5 vol. %.

Samples of the reaction mixture were taken during the reaction at different times. The concentration (in wt. % on the basis of the total reaction mixture) of reaction mixture components was measured by means of gas chromatography, for methyl phenyl carbinol (MPC) and methyl phenyl ketone (MPK), and by means of iodometric titration, for ethylbenzene hydroperoxide (EBHP).

EXAMPLE 1

The experiment of Comparative Example 1 was repeated, except that the ethylbenzene used contained 1.2 wt. % of styrene.

EXAMPLE 2

The experiment of Comparative Example 1 was repeated, except that the ethylbenzene used contained 1.0 wt. % of 4-chlorostyrene.

EXAMPLE 3

The experiment of Comparative Example 1 was repeated, except that the ethylbenzene used contained 1.5 wt. % of 4-t-butylstyrene.

COMPARATIVE EXAMPLE 2

The experiment of Comparative Example 1 was repeated, except that the reactor temperature was 145° C. and the reflux temperature was 80° C.

EXAMPLE 4

The experiment of Comparative Example 2 was repeated, except that the ethylbenzene used contained 1.1 wt. % of styrene.

Experimental Results

Figure 2:
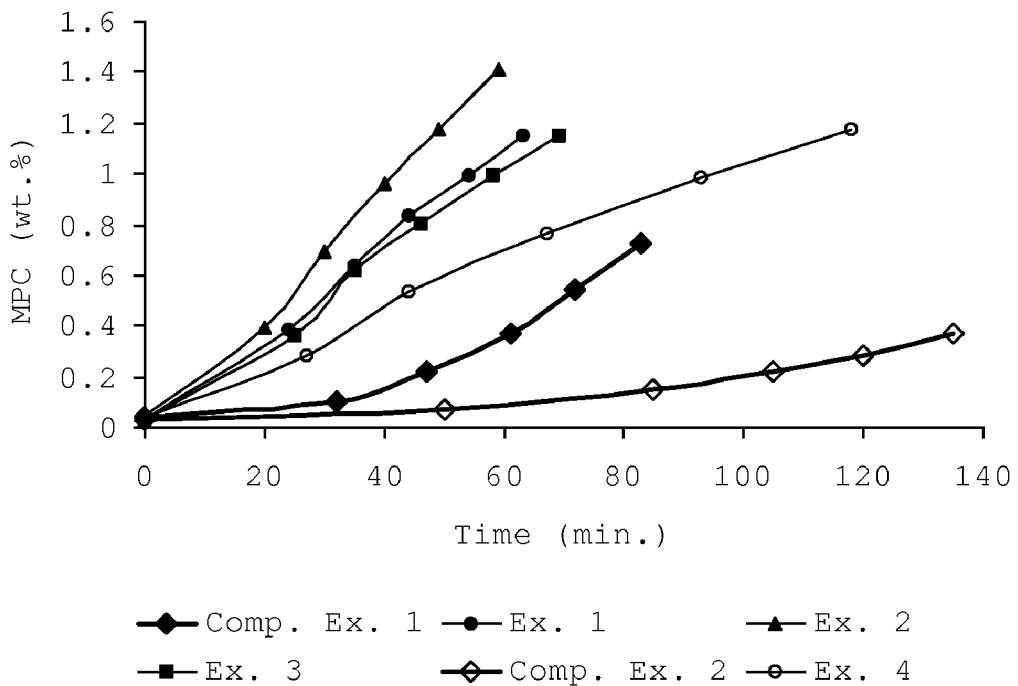
FIG. 2 depicts the production of methyl phenyl carbinol as a function of time.
Figure 3:
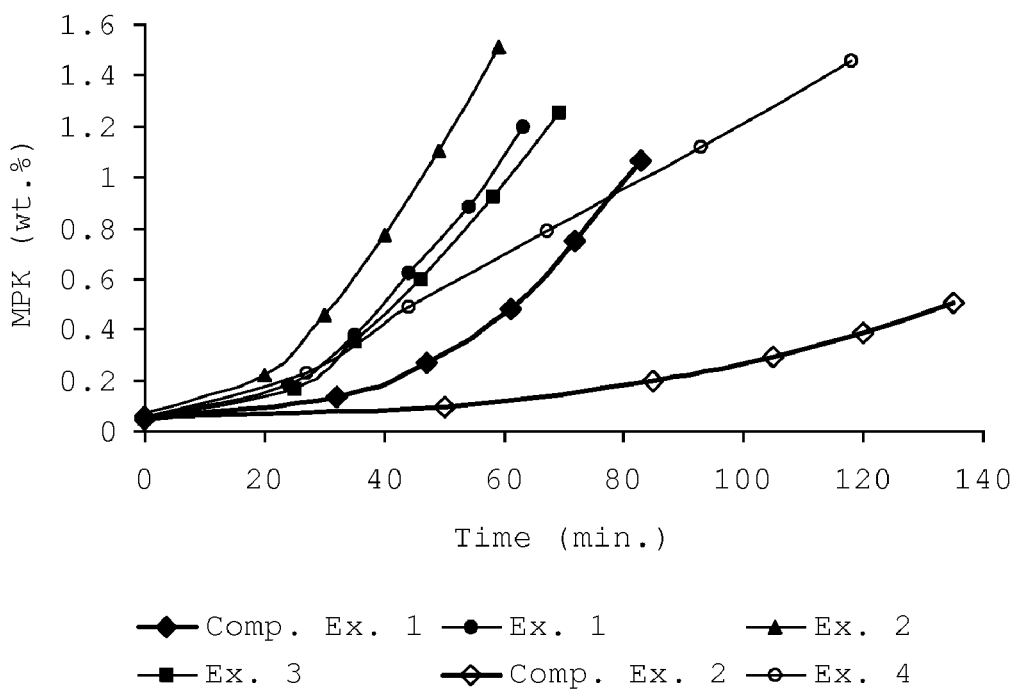
FIG. 3 depicts the production of methyl phenyl ketone as a function of time.

The experimental results of Comparative Examples 1 and 2 and Examples 1-4 are shown in Table 1 and FIGS. 1-3. FIGS. 1-3 show the concentrations of EBHP, MPC and MPK (in wt. % on the basis of the total reaction mixture), respectively, in time (in minutes).

The results show that in the experiments where the reactor temperature was 156° C. and the reflux temperature was 95° C., the addition of only a small amount of styrene already results in a substantially higher EBHP production per time unit. This positive effect on EBHP production is even greater when styrene is replaced by 4-chlorostyrene.

The results for the experiments where the reactor temperature was 145° C. and the reflux temperature was 80° C. show a similar effect, with the proviso that the addition of only a small amount of styrene (i.e. in Example 4) results in an even higher EBHP production per time unit (i.e. in comparison with Example 1) relative to the experiments where no styrene is added (i.e. Comparative Examples 2 and 1, respectively).

The above experiments have shown that the period for reaching a particular EBHP concentration, for example 10 wt. %, is shortened by feeding only a relatively small amount of styrene or a styrene derivative. For example, said EBHP concentration of 10 wt. % is reached within about 56 minutes when 1.0 wt. % of 4-chlorostyrene is fed to the reaction mixture which is about 21% shorter than when no 4-chlorostyrene is fed in which case said EBHP concentration is only reached within 68 minutes.

This shortening of the reaction time (higher reaction rate) is very advantageous. As can be concluded from the experimental results, the EBHP production after a certain lapse of time is substantially higher when a relatively small amount of styrene or a styrene derivative is fed to the reaction mixture. This advantageously results, after a certain lapse of time, in a higher yield of EBHP relative to the amount of ethylbenzene fed.

Further, the experimental results show that by feeding styrene or a styrene derivative, relatively more MPC and MPK are formed. Because of this, the selectivity to ethylbenzene hydroperoxide is in fact decreased. However, MPC and MPK may be advantageously converted into styrene, which is a valuable product. Such production of styrene may for example take place in an integrated process for producing an alkylene oxide (for example propylene oxide) and styrene, for example the SM/PO process, as discussed above.

TABLE 1

| Example no. | time (min.) | EBHP (wt. %) | MPC (wt. %) | MPK (wt. %) |
|---|---|---|---|---|
| Comparative Example 1 | 0 | 0.33 | 0.04 | 0.05 |
| | 32 | 3.37 | 0.11 | 0.13 |
| | 47 | 5.94 | 0.22 | 0.27 |
| | 61 | 8.52 | 0.37 | 0.48 |
| | 72 | 10.77 | 0.54 | 0.75 |
| | 83 | 12.91 | 0.73 | 1.06 |
| Example 1 | 0 | 0.27 | 0.03 | 0.05 |
| | 24 | 2.75 | 0.39 | 0.19 |
| | 35 | 4.88 | 0.64 | 0.38 |
| | 44 | 6.85 | 0.84 | 0.62 |
| | 54 | 8.81 | 0.99 | 0.89 |
| | 63 | 10.42 | 1.15 | 1.20 |
| Example 2 | 0 | 0.36 | 0.04 | 0.07 |
| | 20 | 2.68 | 0.40 | 0.22 |
| | 30 | 4.95 | 0.70 | 0.46 |
| | 40 | 6.94 | 0.96 | 0.77 |
| | 49 | 8.70 | 1.18 | 1.10 |
| | 59 | 10.41 | 1.41 | 1.51 |
| Example 3 | 0 | 0.27 | 0.03 | 0.05 |
| | 25 | 2.39 | 0.37 | 0.17 |
| | 35 | 4.40 | 0.62 | 0.36 |
| | 46 | 6.43 | 0.81 | 0.60 |
| | 58 | 8.43 | 0.99 | 0.92 |
| | 69 | 10.13 | 1.15 | 1.26 |
| Comparative Example 2 | 0 | 0.29 | 0.03 | 0.05 |
| | 50 | 2.04 | 0.07 | 0.09 |
| | 85 | 4.48 | 0.15 | 0.19 |
| | 105 | 6.07 | 0.22 | 0.29 |
| | 120 | 7.46 | 0.28 | 0.38 |
| | 135 | 8.76 | 0.37 | 0.51 |
| Example 4 | 0 | 0.32 | 0.04 | 0.06 |
| | 27 | 2.37 | 0.28 | 0.23 |
| | 44 | 4.29 | 0.54 | 0.49 |
| | 67 | 6.15 | 0.77 | 0.78 |
| | 93 | 7.90 | 0.99 | 1.12 |
| | 118 | 9.42 | 1.18 | 1.46 |

What is claimed:

1. A process for the liquid phase oxidation of ethylbenzene into ethylbenzene hydroperoxide, wherein the ethylbenzene hydroperoxide concentration is kept below 20 wt. % on the basis of the total weight of the reaction mixture, and wherein styrene and/or a styrene derivative is fed to the ethylbenzene.

2. The process as claimed in claim 1, wherein the ethylbenzene hydroperoxide concentration is kept below 15 wt. %.

3. The process as claimed in claim 1, wherein the concentration of styrene and/or a styrene derivative is from 0.01 to 5.0 wt. % on the basis of the total weight of the reaction mixture.

4. The process as claimed in claim 1, wherein styrene is fed to the ethylbenzene.

5. The process as claimed in claim 4, wherein the styrene is fed via a recycle ethylbenzene stream.

6. The process as claimed in claim 1, wherein the styrene derivative is a styrene derivative wherein one or more of the unsubstituted carbon atoms of styrene is or are substituted by an alkyl group and/or a halogen atom.

7. The process as claimed in claim 6, wherein the alkyl group is a straight or branched alkyl group comprising from 1 to 10 carbon atoms.

8. The process as claimed in claim 7, wherein the alkyl group is a methyl, ethyl, n-propyl, i-propyl, n-butyl, s-butyl or t-butyl group.

9. The process as claimed in claim 6, wherein the halogen atom is a chlorine atom.

10. A process for the preparation of an alkylene oxide and styrene, comprising the steps of:
   i) oxidizing ethylbenzene into ethylbenzene hydroperoxide according to a process of claim 1;
   ii) reacting the ethylbenzene hydroperoxide with an alkene to prepare alkylene oxide and methyl phenyl carbinol; and
   iii) dehydrating methyl phenyl carbinol into styrene.

11. The process as claimed in claim 10, wherein the alkene is propylene.

* * * * *